(12) United States Patent
Zheng et al.

(10) Patent No.: US 12,257,458 B2
(45) Date of Patent: Mar. 25, 2025

(54) ULTRASONIC WAKE-UP SYSTEM

(71) Applicant: SHENZHEN INSTITUTES OF ADVANCED TECHNOLOGY CHINESE ACADEMY OF SCIENCES, Shenzhen (CN)

(72) Inventors: Hairong Zheng, Shenzhen (CN); Wei Zhou, Shenzhen (CN); Long Meng, Shenzhen (CN); Lili Niu, Shenzhen (CN); Zhengrong Lin, Shenzhen (CN); Xiaowei Huang, Shenzhen (CN); Junjie Zou, Shenzhen (CN)

(73) Assignee: SHENZHEN INSTITUTES OF ADVANCED TECHNOLOGY CHINESE ACADEMY OF SCIENCES, Shenzhen (CN)

( * ) Notice: Subject to any disclaimer, the term of this patent is extended or adjusted under 35 U.S.C. 154(b) by 85 days.

(21) Appl. No.: 18/325,982

(22) Filed: May 30, 2023

(65) Prior Publication Data
US 2023/0293914 A1   Sep. 21, 2023

Related U.S. Application Data

(63) Continuation of application No. PCT/CN2020/135435, filed on Dec. 10, 2020.

(51) Int. Cl.
*A61N 7/00* (2006.01)
*A61B 8/00* (2006.01)
*A61B 8/08* (2006.01)

(52) U.S. Cl.
CPC .................. *A61N 7/00* (2013.01); *A61B 8/54* (2013.01); *A61B 8/0808* (2013.01); *A61B 8/085* (2013.01); *A61N 2007/0026* (2013.01)

(58) Field of Classification Search
CPC .. A61N 2007/0026; A61M 2021/0038; A61M 2021/0083
See application file for complete search history.

(56) References Cited

U.S. PATENT DOCUMENTS

| | | | | |
|---|---|---|---|---|
| 2011/0178441 | A1* | 7/2011 | Tyler | A61N 5/062 601/2 |
| 2011/0208094 | A1* | 8/2011 | Mishelevich | A61N 7/02 601/2 |

(Continued)

FOREIGN PATENT DOCUMENTS

| | | |
|---|---|---|
| CN | 102149428 A | 8/2011 |
| CN | 109771855 A | 5/2019 |
| CN | 111973894 A | 11/2020 |

*Primary Examiner* — Colin T. Sakamoto
(74) *Attorney, Agent, or Firm* — Nitin Kaushik

(57) ABSTRACT

The present application provides an ultrasonic wake-up system. The system includes an ultrasonic imaging device, an ultrasound stimulation device, and an ultrasound stimulation effect evaluation device, and acquires an ultrasonic image of a target object through the ultrasonic imaging device, transmits an ultrasound to the target object based on the ultrasonic image through the ultrasound stimulation device, and adjusts the transmitted ultrasound required through the ultrasound stimulation effect evaluation device. Therefore, peripheral nerves are accurately stimulated, an uplink reticular wake-up system is activated, so as to wake up patients with disorders of consciousness.

5 Claims, 3 Drawing Sheets

(56) References Cited

U.S. PATENT DOCUMENTS

2014/0343463 A1* 11/2014 Mishelevich ............ A61N 7/00
  601/2
2018/0028841 A1*  2/2018 Konofagou ............ A61B 8/085
2021/0068793 A1*  3/2021 Singanamalli ............ A61B 8/54

* cited by examiner

ULTRASONIC WAKE-UP SYSTEM

TECHNICAL FIELD

The present application relates to the technical field of ultrasound, and in particular, to an ultrasonic wake-up system.

BACKGROUND

At present, for patients with disorders of consciousness, they often stimulate an uplink reticular wake-up system through drugs or wake-up devices to wake up the excitability of related nuclei in the uplink reticular wake-up system, so as to increase an excitement level of cerebral cortex and finally achieve an aim of wake-up.

However, the effect achieved by drug stimulation is very limited and the existing wake-up techniques cannot achieve effective wake-up for characteristics of the patients either.

SUMMARY

The present application provides an ultrasonic wake-up system, which can achieve effective wake-up for characteristics of patients.

Embodiments of the present application provide an ultrasonic wake-up system, including: an ultrasonic imaging device, an ultrasound stimulation device, and an ultrasound stimulation effect evaluation device; where
 the ultrasonic imaging device, the ultrasound stimulation device, and the ultrasound stimulation effect evaluation device are connected with each other;
 the ultrasonic imaging device is configured for acquiring an ultrasonic image of a target object;
 the ultrasound stimulation device is configured for transmitting an ultrasound to the target object based on the ultrasonic image; and
 the ultrasound stimulation effect evaluation device is configured for detecting a physiological signal of the target object, and adjusting the ultrasound based on the physiological signal.

In a specific implementation, an ultrasound stimulation device includes: an ultrasonic parameter selecting unit, an ultrasonic transmitting processing unit, and an ultrasonic transducer unit; where
 the ultrasonic parameter selecting unit is configured for determining an ultrasonic parameter corresponding to the target object, and the ultrasonic parameter is configured for determining a frequency domain characteristic and a time domain characteristic of the ultrasound transmitted to the target object;
 the ultrasonic transmitting processing unit is configured for determining target area information for transmitting the ultrasound to the target object according to the ultrasonic image, and controlling the ultrasonic transducer unit to transmit the ultrasound based on the target area information and the ultrasonic parameter.

Optionally, the ultrasonic parameter selecting unit is specifically configured for:
 determining the ultrasonic parameter based on a physiological characteristic of the target object and/or the target area information.

Optionally, the target area information includes at least one of a size of a target area, a depth of a target area, and a position of a target area.

In a specific implementation, the ultrasonic transducer unit includes: at least one ultrasonic transducer, the ultrasonic transducer including at least one ultrasonic array element;
 the ultrasonic transmitting processing unit is connected with the at least one ultrasonic transducer; and
 the ultrasonic transducer is configured for receiving a first control instruction output by the ultrasonic transmitting processing unit, and controlling at least one ultrasonic array element to send the ultrasound based on the first control instruction.

Optionally, the ultrasonic transmitting processing unit is further configured for:
 determining a deployment location of the ultrasonic transducer unit based on the target area information.

Optionally, the ultrasonic parameter includes: at least one of ultrasonic frequency, ultrasonic duration, ultrasonic intensity, pulse repetition frequency, and duty cycle.

In a specific implementation, the ultrasound stimulation effect evaluation device is specifically configured for:
 adjusting the target area information and the ultrasonic parameter based on the physiological signal.

Optionally, the physiological signal includes: at least one of an electromyographic signal, an electroencephalographic signal, and a behavioral data rating.

Optionally, the ultrasound stimulation effect evaluation device is specifically configured for:
 detecting a basic physiological index of the target object, where the basic physiological index includes: at least one of heart rate, body temperature, and respiration;
 evaluating safety of the ultrasound based on the basic physiological index;
 and when an evaluation result indicates that the safety of the ultrasound is lower than a preset value, sending a second control instruction to the ultrasound stimulation device, where the second control instruction is configured for instructing the ultrasound stimulation device to stop transmitting the ultrasound or adjusting the ultrasonic parameter.

Optionally, the ultrasonic transducer includes: a surface acoustic wave ultrasonic transducer or a bulk wave ultrasonic transducer.

The ultrasonic wake-up system provided by the embodiments of the present application includes the ultrasonic imaging device, the ultrasound stimulation device, and the ultrasound stimulation effect evaluation device, and acquires the ultrasonic image of the target object through the ultrasonic imaging device, transmits the ultrasound to the target object based on the ultrasonic image through the ultrasound stimulation device, and adjusts the transmitted ultrasound required through the ultrasound stimulation effect evaluation device. Therefore, peripheral nerves are accurately stimulated, an uplink reticular wake-up system is activated, so as to wake-up patients with disorders of consciousness.

BRIEF DESCRIPTION OF DRAWINGS

In order to more clearly explain technical solutions in embodiments of the present application or the prior art, the following will briefly introduce drawings needed in the description of the embodiments or the prior art. Obviously, the drawings in the following description are some embodiments of the present application. For those of ordinary skill in the art, other drawings can be obtained according to these drawings without any creative effort.

DETAILED DESCRIPTION OF THE EMBODIMENTS

Figure 1:
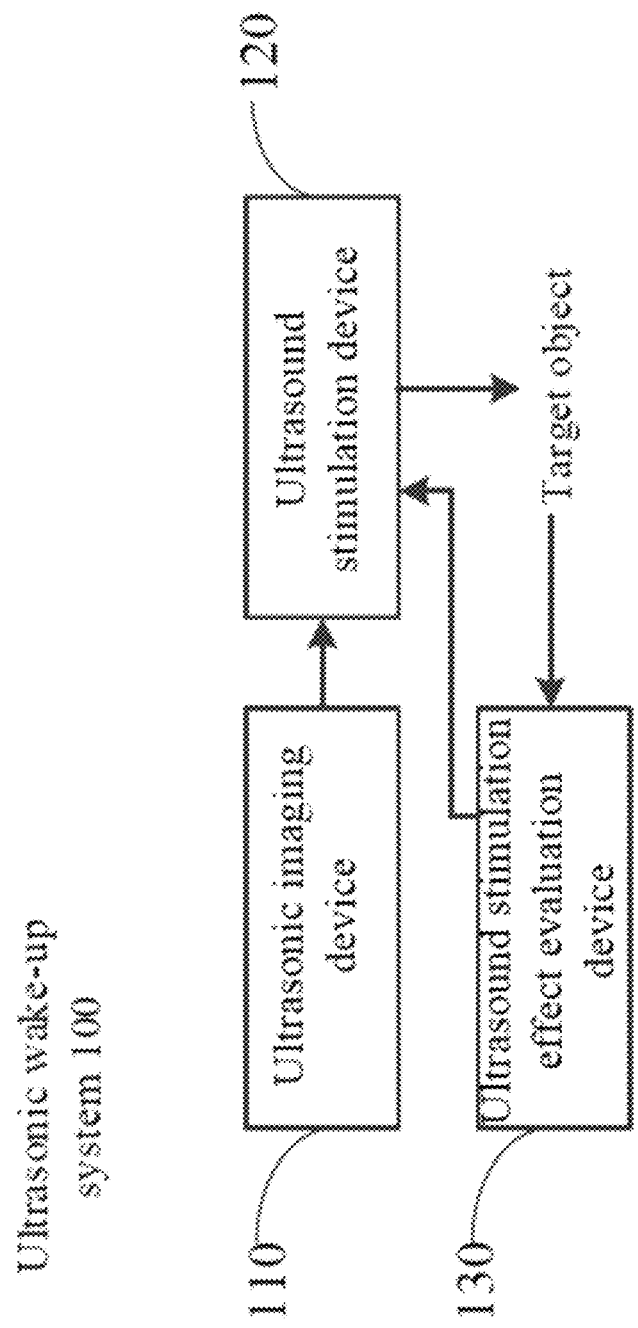
FIG. 1 is a schematic structural diagram of an ultrasonic wake-up system 100 according to the embodiments of the present application.

In order to make objectives, technical solutions and advantages of embodiments of the present application more clear, the technical solutions in the embodiments of the present application will be described clearly and completely with reference to the drawings in the embodiments of the present application, and it is obvious that the described the embodiments are some embodiments of the present application, and not all embodiments. All other embodiments acquired by those of ordinary skilled in the art based on the embodiments in the present application without making any creative labor fall within the protection scope of the present application.

Disorders of consciousness (DOC) in clinic mainly include somnolence, lethargy, coma, confusion, delirium state, cerebral cortex removed state and vegetative state. Patients (as target objects in the following) usually recover from a brief coma, but some suffer from long-term disorders of consciousness. For example, vegetative state, unresponsive awakening syndrome, persistent vegetative state, or micro-conscious state. In order to wake up a patient with long-term disorders of consciousness, the excitability of related nuclei in an uplink reticular wake-up system is increased by drug stimulation, such as Amantadine (Amantadine), intrathecal baclofen (intrathecal baclofen), midazolam (midazolam), ziconotide (ziconotide), transcranial electrical stimulation, transcranial magnetic stimulation, vagus nerve stimulation, spinal stimulation, so as to increase an excitement level of cerebral cortex and finally achieve an aim of wake-up.

In recent years, with the continuous development of ultrasound technologies, ultrasonic neuromodulation can non-invasively penetrate through a skull to regulate and control nerve nuclei of a brain, and researches show that the ultrasound can realize the regulation and control of peripheral nerves, the peripheral nerves are stimulated by means of utilizing the ultrasonic neuromodulation, and signal input of the uplink reticular wake-up system is increased, so as to achieve wake-up of the patients with the disorders of consciousness. However, the existing wake-up technologies cannot achieve non-invasive stimulation on deep nerves of the human body, the stimulation of the deep nerves requires implantation, such that the patients are traumatic, positions of implanted electrodes are fixed, stimulation positions cannot be changed in real time according to a stimulation effect of the patients due to a fact that different peripheral nerves of different patients have different sensitivities to ultrasonic stimulation, causing that a targeted treatment of the patients cannot be achieved, and a wake-up effect is poor.

In view of the above technical problems, the ultrasonic wake-up system provided in the embodiments of the present application can acquire an ultrasonic image of a target object through an ultrasonic imaging device, and transmit an ultrasound to the target object based on the acquired ultrasonic image through an ultrasound stimulation device, and then detect a physiological signal of the target object, and adjust the ultrasound based on a physiological signal through an ultrasound stimulation effect evaluation device, achieving the effective wake-up of the target object.

FIG. 1 is a schematic structural diagram of an ultrasonic wake-up system 100 according to the embodiments of the present application. As shown in FIG. 1, an ultrasonic wake-up system 100 includes: an ultrasonic imaging device 110, an ultrasound stimulation device 120, and an ultrasound stimulation effect evaluation device 130.

The ultrasonic imaging device 110, the ultrasound stimulation device 120, and the ultrasound stimulation effect evaluation device 130 are connected with each other.

Where the ultrasonic imaging device 110 is configured for acquiring an ultrasonic image of a target object. Generally, the ultrasonic image should include peripheral nerve data of the target object, such as vagus nerve, median nerve, sciatic nerve.

The ultrasound stimulation device 120 transmits a corresponding ultrasound to the target object by analyzing the ultrasonic image based on the ultrasonic image acquired by the ultrasonic imaging device 110.

Optionally, in the embodiments of the present application, the ultrasound transmitted by the ultrasound stimulation device 120 may act on all nervous systems except for cranial nerves and a spinal nervous system.

The ultrasound stimulation effect evaluation device 130 is configured for detecting a physiological signal of the target object, and adjusting the ultrasound based on the physiological signal.

Figure 2:
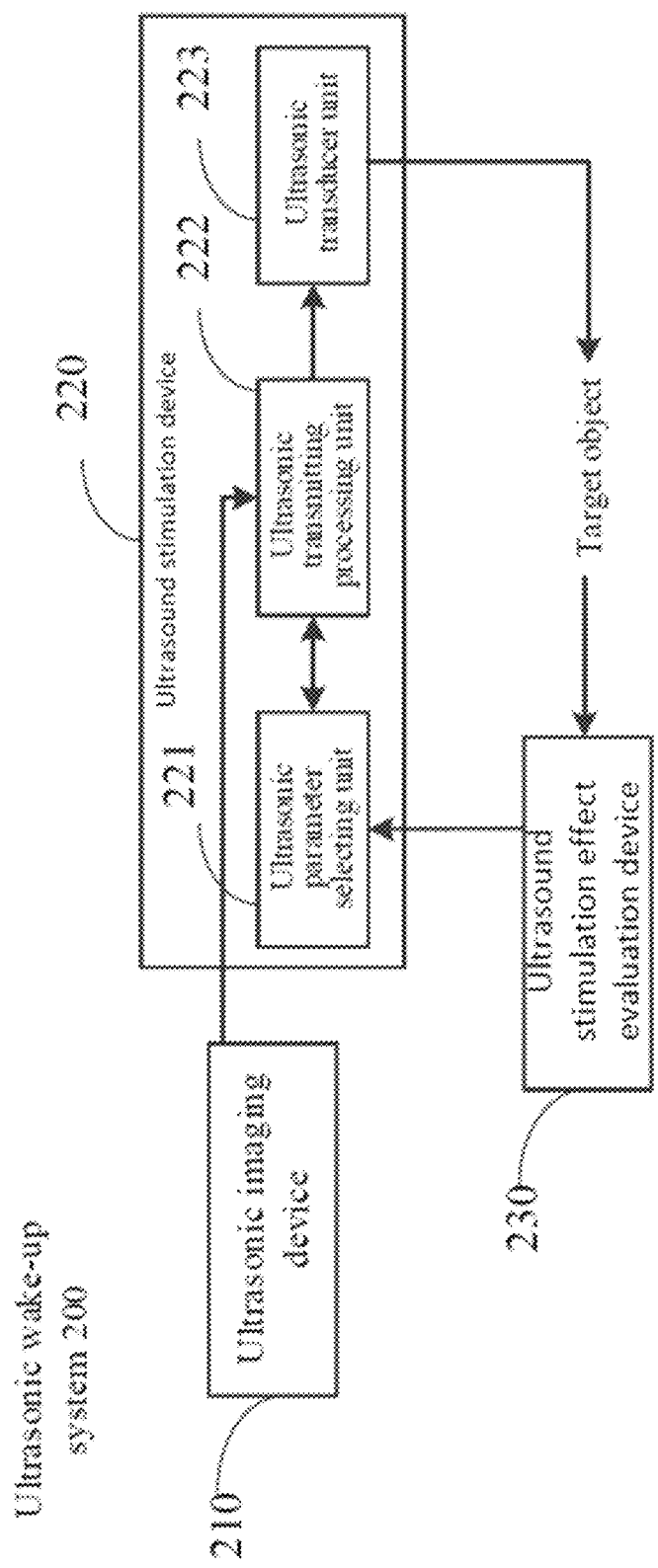
FIG. 2 is a schematic structural diagram of an ultrasonic wake-up system 200 according to the embodiments of the present application.

FIG. 2 is a schematic structural diagram of an ultrasonic wake-up system 200 according to embodiments of the present application.

In order to enable the ultrasonic wake-up system to wake up a target object more accurately and effectively through the ultrasound transmitted by the ultrasound stimulation device and/or a target area of the transmitted ultrasound.

In combined with and as shown in FIG. 2, the ultrasound stimulation device 220 in the ultrasonic wake-up system 200 includes: an ultrasonic parameter selecting unit 221, an ultrasonic transmitting processing unit 222, and an ultrasonic transducer unit 223.

Illustratively, the ultrasonic transmitting processing unit 222 is connected with the ultrasonic parameter selecting unit 221 and the ultrasonic transducer unit 223, respectively.

Illustratively, the ultrasonic transmitting processing unit 222 is connected with the ultrasonic imaging device 210, and the ultrasonic parameter selecting unit 221 is connected with the ultrasound stimulation effect evaluation device 230.

Where the ultrasonic parameter selecting unit 221 is configured for determining an ultrasonic parameter corresponding to the target object, and the ultrasonic parameter is configured for determining a frequency domain characteristic and a time domain characteristic of the ultrasound transmitted to the target object.

The ultrasonic transmitting processing unit 222 is configured for determining target area information for transmitting the ultrasound to the target object according to the ultrasonic image, and controlling the ultrasonic transducer unit to transmit the ultrasound based on the target area information and the ultrasonic parameter.

It should be noted that the target area information includes at least one of a size of a target area, a depth of a target area, and a position of a target area.

Illustratively, the ultrasonic transmitting processing unit 222 determines at least one of a size of a target area, a depth of a target area, and a position of a target area to the target object based on the ultrasonic image. It should be understood that the target area corresponds to peripheral nerves in the uplink reticular wake-up system.

In a specific implementation, the ultrasonic parameter selecting unit 221 determines the ultrasonic parameter based on a physiological characteristic of the target object and/or the target area information. Illustratively, a plurality of groups of ultrasonic parameters can be preset, corresponding to different physiological characteristics of the target object and target area information of the target area on which the ultrasound is to act, and a corresponding ultrasonic parameter can be found through table lookup; or based on the physiological characteristic of the target object and the target area information of the target area on which the ultrasound is to act, a corresponding ultrasonic parameter can be calculated according to a preset function.

Optionally, the physiological characteristic of the target object includes at least one of age, sex, and disease of the target object.

Optionally, the ultrasonic parameter can determine an ultrasonic stimulation mode and energy based on the physiological characteristic of the target object.

In the embodiments of the present application, the ultrasonic wake-up system 200 determines the target area information to be acted on by the ultrasound for the ultrasonic image of the target object through the ultrasonic transmitting processing unit 222, and determines the ultrasonic parameter corresponding to the target object based on the actual physiological characteristic and/or target area information of the target object through the ultrasonic parameter selecting unit 221, and then controls the ultrasonic transducer unit 223 to transmit the corresponding ultrasound to the target object in the corresponding target area through the ultrasonic transmitting processing unit 222, in order to achieve the effective wake-up of the target object.

Figure 3:
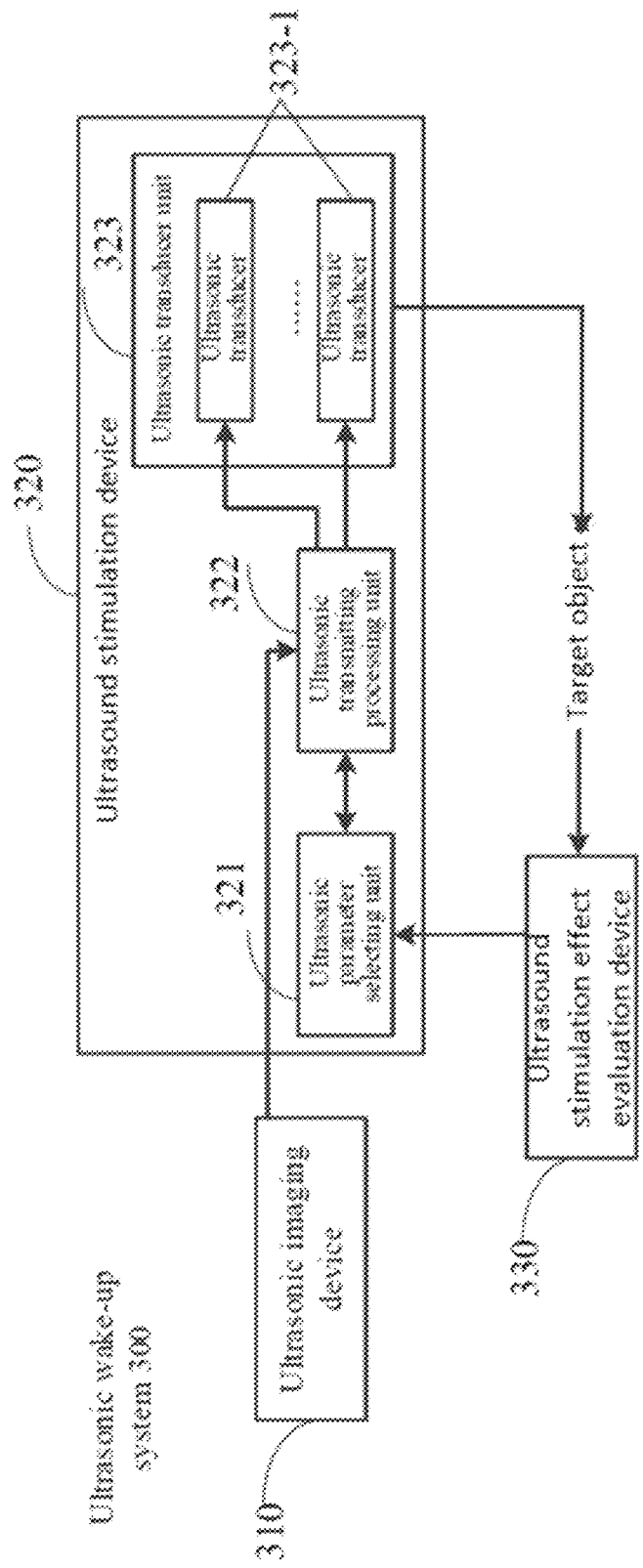
FIG. 3 is a schematic structural diagram of an ultrasonic wake-up system 300 according to the embodiments of the present application.

FIG. 3 is a schematic structural diagram of an ultrasonic wake-up system 300 according to the embodiments of the present application.

In combined with and as shown in FIG. 3, in order to enable the ultrasonic wake-up system to have a better wake-up capability, the ultrasonic transducer unit 323 of the ultrasonic wake-up system 300 is provided with an ultrasonic transducer 323-1, and the number of the ultrasonic transducers 323-1 is one to more. Generally, the greater the number of the ultrasonic transducers 323-1, the more easily the transmitted ultrasound can be controlled, and when the number of the ultrasonic transducers 323-1 is more, the ultrasonic transducer unit 323 is an ultrasonic transducer array.

At least one ultrasonic array element is deployed in each ultrasonic transducer, where the ultrasonic array element is configured for transmitting the ultrasound.

Optionally, the ultrasonic transducer may be a surface acoustic wave ultrasonic transducer or a bulk wave ultrasonic transducer.

The ultrasonic transmitting processing unit 322 is connected with at least one ultrasonic transducer 323-1 in the ultrasonic transducer unit 323.

Each ultrasonic transducer 323-1 is configured for receiving a first control instruction output by the ultrasonic transmitting processing unit 322. It should be understood that the first control instruction is configured for instructing the ultrasonic transducer 323-1 to control at least one ultrasonic array element that is deployed to transmit a corresponding ultrasound, and further, each ultrasonic transducer 323-1 controls at least one ultrasonic array element to transmit the ultrasound based on the first control instruction.

In the embodiments of the present application, the ultrasonic wake-up system 300 controls at least one ultrasonic specialist 323-2 to generate and transmit a corresponding ultrasound based on the first control instruction of the ultrasonic transmitting processing unit 322 through at least one ultrasonic transducer 323-1 provided in the ultrasonic transducer unit 323.

In one possible implementation, the ultrasonic transmitting processing unit 322 is further configured for: determining a deployment location of the ultrasonic transducer unit 323 based on the target area information. Illustratively, the ultrasonic transmitting processing unit 322 determines the deployment position of the ultrasonic transducer unit 323 according to a position of the target area in the target area information. Illustratively, the ultrasonic wake-up system 300 controls the ultrasonic transducer unit 323 to move to a corresponding deployment position and fix it through the ultrasonic transmitting processing unit 322 or any other processing unit.

It should be understood that the ultrasonic parameter determined by the ultrasonic parameter selecting unit in any one of embodiments of FIGS. 1 to 3 includes: at least one of ultrasonic frequency, ultrasonic duration, ultrasonic intensity, pulse repetition frequency, and duty cycle.

In a specific implementation, the ultrasound stimulation effect evaluation device in any one of embodiments of FIGS. 1 to 3 is specifically configured for: adjusting the target area information and the ultrasonic parameter based on the physiological signal.

Illustratively, the ultrasound stimulation effect evaluation device detects the physiological signal of the target object in real time before and during wake-up of the ultrasonic wake-up system 300. Illustratively, the physiological signal includes: at least one of an electromyographic signal, an electroencephalographic signal, and a behavioral data rating.

In a specific implementation, the ultrasound stimulation effect evaluation device in any one of embodiments of FIGS. 1 to 3 is further configured for:

detecting a basic physiological index of the target object, and it should be understood that the basic physiological index includes at least one of heart rate, body temperature, and respiration.

Further, safety of the ultrasound is evaluated based on the basic physiological index. For example, if the heart rate is lower than a lower threshold of the heart rate or higher than an upper threshold of the heart rate, or the body temperature is lower than a lower threshold of the body temperature or higher than an upper threshold of the body temperature, which indicates that life safety of the target object may be affected by the ultrasound being transmitted to the target object, the transmitted ultrasound needs to be controlled in time to improve the safety of the ultrasound during a transmitting process.

Further, when an evaluation result indicates that the safety of the ultrasound is lower than a preset value, a second control instruction is sent to the ultrasound stimulation device, and the second control instruction is configured for instructing the ultrasound stimulation device to stop transmitting the ultrasound or adjusting the ultrasonic parameter, for example, adjusting the ultrasonic parameter to enable the ultrasound transmitted by the ultrasound stimulation device to have at least one of a low ultrasonic frequency, a low ultrasonic intensity or a reduced ultrasonic duration.

In summary, the ultrasonic wake-up system provided by the application can provide a non-invasive and safe ultrasonic peripheral nerve wake-up effect for the patients with the disorders of consciousness, can accurately stimulate the peripheral nerve at each position, effectively increase input of the uplink reticular wake-up system, so as to activate the cerebral cortex to achieve the wake-up. And since coma can be divided into a plurality of grades, the ultrasonic wake-up system in the present application can evaluate the grade of the coma by a method of acquiring the electroencephalogram signal and the electromyogram signal, and the present application can be compatible with functional magnetic resonance and positron computer-emitted tomography (PET) for collaborative evaluation, and finally adjusts the ultrasonic parameter and the target area of ultrasonic wake-up through the evaluated result, so as to optimize an ultrasonic wake-up effect.

It should be understood that any one of the processing units in the embodiments of the present application may be an integrated circuit chip having signal processing capability. During the implementation, each step of the above embodiments may be implemented by an integrated logic circuit of hardware in a processor or by an instruction in a form of software. The above processing unit may be a processor, a digital signal processor (DSP), an application specific integrated circuit (ASIC), a field programmable gate array (FPGA) or other programmable logic devices, a discrete component gate or a transistor logic device, a discrete hardware component and the like. Each step disclosed in the embodiments of the present application may be achieved or performed. A general-purpose processor may be a microprocessor or the processor may be any conventional processor or the like. The content disclosed in the embodiments of the present application may be directly implemented by a hardware decoding processor, or implemented by a combination of hardware and software modules in a decoding processor. Optionally, the ultrasonic wake-up system according to the embodiments of the present application is provided with a memory, or each device in the ultrasonic wake-up system is provided with the memory, and a software module may be located in a mature storage medium in the art, such as a random access memory, a flash memory, a read-only memory, a programmable read-only memory, or an electrically erasable programmable memory, and a register. The storage medium is located in the memory, and the processor reads information in the memory and completes the above embodiments in combination with the hardware thereof.

It could be understood that the memory in the embodiments of the present application can be either volatile memory or non-volatile memory, or can include both volatile and non-volatile memory. Where the non-volatile memory may be a read-only memory (ROM), a programmable ROM (PROM), an erasable PROM (EPROM), an electrically EPROM (EEPROM), or a flash memory. The volatile memory may be a random access memory (RAM) which serves as an external cache. By way of example, and not limitation, many forms of RAM are available, such as a static random access memory (SRAM), a dynamic random access memory (DRAM), a synchronous DRAM (SDRAM), a double data rate SDRAM (DDR SDRAM), an enhanced SDRAM (ESDRAM), a synchlink DRAM (SLDRAM), and a direct rambus RAM (DR RAM). It should be noted that the memory of the system and method described herein is intended to include, without being limited to, these and any other suitable types of memory.

It should be understood that the above memory is illustratively but not limiting, for example, the memory in the embodiments of the present application may also be a static RAM (SRAM), a dynamic RAM (DRAM), a synchronous DRAM (SDRAM), a double data rate SDRAM (DDR SDRAM), an enhanced SDRAM (ESDRAM), a synchlink DRAM (SLDRAM), and a direct rambus RAM (DR RAM) and the like. That is, the memory in the embodiments of the present application is intended to include, without being limited to, these and any other suitable types of memory.

The embodiments of the present application further provide a computer-readable storage medium for storing a computer program.

Optionally, the computer-readable storage medium may be applied to each device in the ultrasonic wake-up system provided in the embodiments of the present application, and the computer program enables a computer to execute a corresponding process in the embodiments of the present application, which is not described herein again for brevity.

The computer-readable storage medium in the embodiments may be any available medium that can be accessed by a computer, or a data storage device such as a server, a data center, that is integrated with one or more available media, and the available medium may be a magnetic medium (such as a floppy disk, a hard disk, a magnetic tape), an optical medium (such as a DVD), or a semiconductor medium (such as an SSD).

Those of ordinary skill in the art may understand that all or part of the content of the above embodiments may be implemented by hardware associated with an program instruction. The foregoing program may be stored in a computer-readable storage medium. When the program is executed, the content including the above embodiments is executed; and the foregoing storage medium includes: various media that can store a program code, such as ROM, RAM, magnetic or optical disks.

The embodiments of the present application further provide a computer program product containing an instruction, which when run on a computer, causes the computer to execute the content of any one of the above embodiments.

Those of ordinary skill in the art may understand that all or part of steps for achieving the above embodiments may be implemented by hardware, or may be implemented by instructing relevant hardware through a program, where the program may be stored in a computer-readable storage medium, and the above storage medium may be a read-only memory, a magnetic disk or an optical disk.

The above description is only the preferred embodiments of the present application and should not be taken as limiting the present application, and any modifications, equivalents, improvements and the like that are made within the spirit and principle of the present application should be included in the protection scope of the present application.

What is claimed is:

1. An ultrasonic wake-up system, comprising: an ultrasonic imaging device, an ultrasound stimulation device, and an ultrasound stimulation effect evaluation device; wherein
the ultrasonic imaging device, the ultrasound stimulation device, and the ultrasound stimulation effect evaluation device are connected with each other;
the ultrasonic imaging device is configured for acquiring an ultrasonic image of a target object;
the ultrasound stimulation device is configured for transmitting an ultrasound to the target object based on the ultrasonic image; and
the ultrasound stimulation effect evaluation device is configured for detecting a physiological signal of the target object and adjusting the ultrasound based on the physiological signal;
wherein the ultrasound stimulation device comprises an ultrasonic parameter selecting unit, an ultrasonic transmitting processing unit and an ultrasonic transducer unit, the ultrasonic parameter selecting unit is configured for determining an ultrasonic parameter corresponding to the target object, and the ultrasonic parameter is configured for determining a frequency domain characteristic and a time domain characteristic of the ultrasound transmitted to the target object;

wherein the ultrasonic transmitting processing unit is configured for determining a depth of a target area for transmitting the ultrasound to the target object according to the ultrasonic image, determining a deployment location of the ultrasonic transducer unit based on the depth of the target area, and controlling the ultrasonic transducer unit to transmit the ultrasound based on the depth of the target area and the ultrasonic parameter; and wherein the ultrasound stimulation effect evaluation device is configured for adjusting the depth of the target area and the ultrasonic parameter based on the physiological signal, and the physiological signal comprises at least one of an electromyographic signal, an electroencephalographic signal, and a behavioral data rating.

2. The system according to claim 1, wherein the ultrasonic parameter selecting unit is specifically configured for:
determining the ultrasonic parameter based on a physiological characteristic of the target object and/or the target area information.

3. The system according to claim 1, wherein the ultrasonic transducer unit comprises: at least one ultrasonic transducer, the ultrasonic transducer comprising at least one ultrasonic array element;

the ultrasonic transmitting processing unit is connected with the at least one ultrasonic transducer; and the ultrasonic transducer is configured for receiving a first control instruction output by the ultrasonic transmitting processing unit, and controlling at least one ultrasonic array element to send the ultrasound based on the first control instruction.

4. The system according to claim 1, wherein the ultrasonic parameter comprises: at least one of ultrasonic frequency, ultrasonic duration, ultrasonic intensity, pulse repetition frequency, and duty cycle.

5. The system according to claim 1, wherein the ultrasound stimulation effect evaluation device is further configured for:
detecting a basic physiological index of the target object, wherein the basic physiological index comprises: at least one of heart rate, body temperature, and respiration;
evaluating safety of the ultrasound based on the basic physiological index;
and when an evaluation result indicates that the safety of the ultrasound is lower than a preset value, sending a second control instruction to the ultrasound stimulation device,
wherein the second control instruction is configured for instructing the ultrasound stimulation device to stop transmitting the ultrasound or adjusting the ultrasonic parameter.

* * * * *